United States Patent
Bahan

[11] Patent Number: 5,941,707
[45] Date of Patent: Aug. 24, 1999

[54] PRECISION ATTACHMENT FOR A PARTIAL DENTURE

[76] Inventor: Kiosegian Bahan, c/o V. Manzikas, POB 3884, 102 10, Piraeus, Greece

[21] Appl. No.: 08/974,645

[22] Filed: Nov. 19, 1997

[30] Foreign Application Priority Data

Apr. 9, 1997 [GR] Greece ............................... 970100132

[51] Int. Cl.$^6$ ..................................... A61C 13/12
[52] U.S. Cl. ........................................... 433/177; 433/183
[58] Field of Search .................................. 433/177, 181, 433/182, 183

[56] References Cited

U.S. PATENT DOCUMENTS

| | | | |
|---|---|---|---|
| 3,535,787 | 10/1970 | Korte | 433/183 |
| 3,787,975 | 1/1974 | Zuest | 433/183 |
| 3,990,150 | 11/1976 | Giovannini | 433/177 |
| 4,259,073 | 3/1981 | Emmons | 433/177 |

*Primary Examiner*—John J. Wilson

[57] ABSTRACT

A precision attachment for a partial denture is described comprising a male portion 1 mounted onto the partial denture with an end extending horseshoe shaped anchorage means 7 comprising a pair of jaws 7a, 7b and a female portion 2 fixedly mounted around a crown 13 surrounding at least one supporting tooth, wherein female portion 2 comprises a pair of parallel side walls 2a, 2b forming a receiving cavity for the anchorage means 7 of male portion 1. Parallel side walls 2a, 2b are interconnected by a spacer pin 5 which is tightly held by jaws 7a, 7b of anchorage means 7 during insertion in place of the partial denture. A partial denture of the invention is thus disclosed with unilateral anchorage, the sole supporting means being the proposed precision attachment, whereby the partial denture can move only in one direction exhibiting a vertical upward-downward movement of its free end during mastication and thereby relieving from stresses applied onto the supporting teeth.

5 Claims, 6 Drawing Sheets

PRECISION ATTACHMENT FOR A PARTIAL DENTURE

THE FIELD OF THE INVENTION

The present invention relates to the field of the art of dentistry and dental craft and in particularly aims at providing a precision attachment for a partial denture with unidirectional freedom of movement effecting a strain-absorber activity, wherein the partial denture is supported with unilateral anchorage, the sole supporting means being the proposed precision attachment.

THE BACKGROUND OF THE INVENTION

In the field of the art of dentistry and dental craft, partial dentures are well known dental fixtures used in replacement of one and more often more lost teeth, being supported by available teeth and mounted onto the alveolar ridge. By replacing lost teeth, partial dentures aim at restoration of the partially lost function of mastication and speech, at preserving and improving the health of soft mouth tissues, at effecting an aesthetic appearance and at improving the overall health of the user.

Typically, a partial denture comprises the base or bases, major and minor connectors, direct and indirect retaining means and a plurality of artificial teeth. Whatever, the category of classification or partial dentures, i.e. whether the partial denture aims at filling with teeth an edentulous area on a single mouth side or on either side thereof, partial dentures need to be adequately supported, retained and stabilized, both horizontally and vertically, against forces applied during mastication or weight forces or forces due to adhesion of food or to stresses arising during speech, cough, laugh, etc. Partial denture supporting, retaining and stabilizing is thereby effected by means of connectors, such as the broadly used palatal bars extending all the way through from one end to the other end of the oral cavity. These connectors are obviously not comfortable for the user. However, the state of the art of partial dentures has not provided a solution to the aforementioned problem and even in the case of a single-sided partial denture such connecting means have to extend all the way through the oral cavity from one side to the other to adequately support the partial denture.

It is therefore the first main object of the present invention to provide an alternative method of supporting a partial denture with unilateral anchorage and thereby eliminate the undesirable, uncomfortable connecting means, which in accordance with prior art method and techniques necessarily extend all the way through, from one side to the other side of the oral cavity.

Satisfying of the above main object of the invention, brings forward the object to provide a new type of precision attachment, classified within the general category of direct retaining means of the prior art, but with substantial advantages over the latter, as will become apparent herein after.

Direct retaining means of the prior art are those parts of the partial denture, which are applied in a certain manner, intracoronal or extracoronal, upon the supporting teeth and retain the partial denture thereon.

Precision attachments are a special type of direct retaining means and comprise a female portion which is retained in an inlay within the anatomical crown or is embodied within an artificial golden crown and a male portion which is mounted onto the base of the partial denture, wherein insertion of the partial denture and retaining of the same is effected by interconnection of the male and female portions of the precision attachment.

Retention capacity of such a precision attachment is dependent upon frictional forces between aforementioned male and female portions, these forces exerting, according to the design of the attachment, suitable, required resistance to the displacement forces exerted onto the partial denture. However, such attachments of the prior art are fixedly connected to the base of the partial denture, such inflexible connection not allowing any movement of the attachment independently of the base of the partial denture.

Aiming at reduction of forces exerted during mastication onto supporting teeth of the partial denture and at a more even distribution of stresses exerted by the denture onto soft mouth tissues, as well as at inhibiting undesired twisting or inclining of teeth of the partial denture, attachments have been designed which are flexibly connected to the base of the partial denture, thereby performing a strain absorbing activity, i.e. acting so as to reduce stresses applied onto the supporting teeth. A broad variety of such precision attachments has been developed and is commercially available. Precision attachments amongst this variety differ with respect to the extent of allowance of movement of the direct retaining means with respect to the base of the partial denture.

Precision attachments of the prior art incorporating such a strain absorbing activity are often complicated accessories with a movable male portion consisting of a plurality of parts which increase cost of the attachment and require a substantially high accuracy for their assembling. Furthermore, none of the precision attachments of the prior art can offer the ability of unilateral anchorage of a partial denture, since construction of these attachments is such that, if the attachment were to be used without retaining means on the other side, it would allow freedom of movement in at least two directions, i.e. displacement of the male relatively to the female portion, namely freedom of rotation of the male within the female portion, such rotation resulting to sideways displacement of the entire partial denture. Moreover, connection of the male and female portions in precision attachments of the prior art—if without retaining means on the other side of the oral cavity—would cause increased stresses because of the forces developing during mastication or related forces due to muscular stresses (cough, laugh, etc.). Thus, precision attachments of the prior art, either those with strain absorbing capacity or those without, require supporting of the partial denture via retaining means at the other side of the oral cavity, which result to the undesired, uncomfortable to feel provision of connectors, such as palatal bars extending all the way along the oral cavity, from one side to the other.

It is therefore an object of the present invention to effectively overcome disadvantages and drawbacks of the prior art and provide a precision attachment for a partial denture with unidirectional freedom of movement, which ensures adequate supporting of the partial denture with unilateral anchorage, thereby eliminating the undesired connecting elements of the prior art, this precision attachment further incorporating a strain absorber capacity, allowing such movements of the partial denture which contribute towards eliminating stresses due to forces developing during mastication and entirely inhibiting sideways movement of the partial denture, which is the decisive factor forcing prior art to employ retaining means on either side of the oral cavity.

Because of the necessity of retaining means on either side of the oral cavity for partial dentures of the prior art, making such partial dentures, irrespective of the type of retaining means (connectors or clasps), requires a substantial fine quality work of the dentist in cooperation with the dental technician and many repetitive visits of the patient to the dentist. Partial dentures of the prior art further require more teeth of the patient to be employed in a supporting role. Obviously, the above substantially increase the cost of the partial denture.

Furthermore, when the need arises for maintenance, repair and partial replacement work of the partial denture and in particular if the precision attachment employed in connection thereto needs to be replaced, the patient has again to undergo repetitive, uncomfortable and costly visits to the dentist for repairing the damage. In this respect it is well known that conventional connectors of the prior art are often apt to wear and loss of their retaining capacity due to frictional contact of male and female portions thereof.

It is therefore a further object of the present invention to disclose such a manner of interconnecting parts of the proposed precision attachment on the one side onto supporting tooth and on the other side onto the partial denture, so that maintenance or even replacement due to wear of the attachment may be made possible without the repetitive, costly and uncomfortable visits of the patient to the dentist for restoring the damage.

It is further well known and obvious that partial dentures of the prior art with the multiple connecting elements and retaining means are complex structures and because of that necessitate following a strictly defined insertion path with a plurality of supporting points and thus it is difficult for the user to insert the partial denture, especially when he is old aged and lacks the ability of performing the highly accurate movements required. Thus, it is often noted that required periodical cleaning and maintenance of the partial denture is not done in accordance with requirements.

It is therefore an object of the present invention to provide a partial denture equipped with the precision attachment of the invention, which has a strain absorber capacity the partial denture being thereby supported with unilateral anchorage, the sole means of anchorage thereof being the proposed precision attachment, the partial denture being easily detachable and easily reinserted into the user's mouth, since it does not require following a strictly defined insertion path, but requires locating a single supporting point only.

These and other objects, characteristics and merits of the present invention will be made apparent in the detailed description following hereinafter.

BRIEF DESCRIPTION OF THE DRAWINGS

The invention will be made apparent to those skilled in the art by reference to the accompanying drawings wherein the invention is depicted in an illustrative and not confining manner.

FIG. 1 shows a perspective view of the precision attachment for a partial denture of the invention dismantled in the two parts it consists of.

DETAILED DESCRIPTION OF PREFERRED EMBODIMENTS

Figure 2:
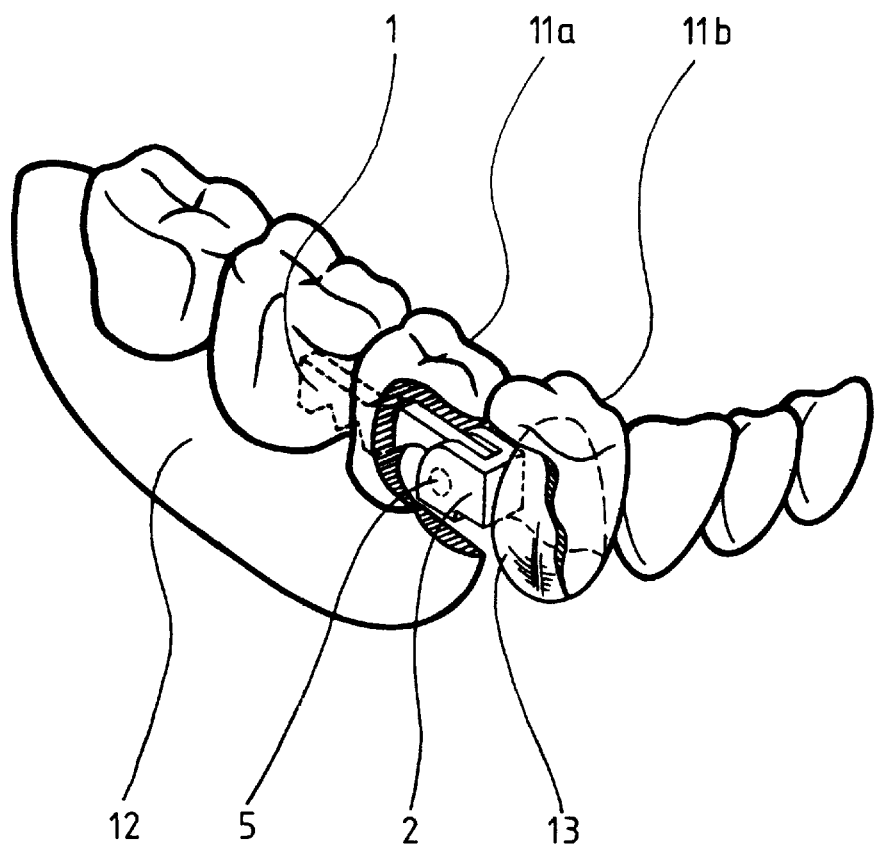
FIG. 2 shows a perspective view of the precision attachment of the invention used with a typical partial denture.

By reference to the accompanying drawings herein below will be described illustrative, non confining embodiments of the invention. The attachment for a partial denture of the invention consists of two portions, the male portion 1 and the female portion 2. As shown in FIG. 2, female portion 2 is fitted within a suitable crown 13 around supporting tooth 11b, whereas male portion 1 is fitted within the frontal portion, i.e. within the depicted frontal tooth 11a of the partial denture. The crown 13 within which fits the female portion 2 of the attachment of the invention may be a simple crown, i.e. mounted onto a single tooth or a twin crown, i.e. mounted onto a pair of two neighboring teeth or a multiple crown, mounted onto an artificial bridge or a suitably designed projecting means. A twin or multiple crown is particularly recommended for partial dentures of the maxilla, wherein vertically downward acting gravitational forces of the weight of the partial denture itself must also be taken into account. Usage of the attachment of the invention and of partial dentures using and being supported by the same is particularly recommended in cases where the supporting tooth is the canine or other tooth rearwards the canine tooth.

The female portion 2 forming a receiving cavity for male portion 1 is a generally II section comprising a pair of parallel side walls 2a, 2b interconnected by laterally extending wall 2c, which is fixedly connected onto crown 13 disposed around one or more supporting teeth. Whereas the upper sides of parallel side walls 2a, 2b follow a uniform curvature, the lower sides thereof are cut to provide uniform curved recessions 6 by means of which contact of parallel side walls 2a, 2b with the gums is inhibited and thereby the gums underneath female portion 2 of the proposed attachment are protected.

A characterizing feature of female portion 2 of the attachment of the invention is a spacer pin 5 which extends laterally within the receiving cavity of female portion 2, interconnecting parallel side walls 2a, 2b.

Figure 1:
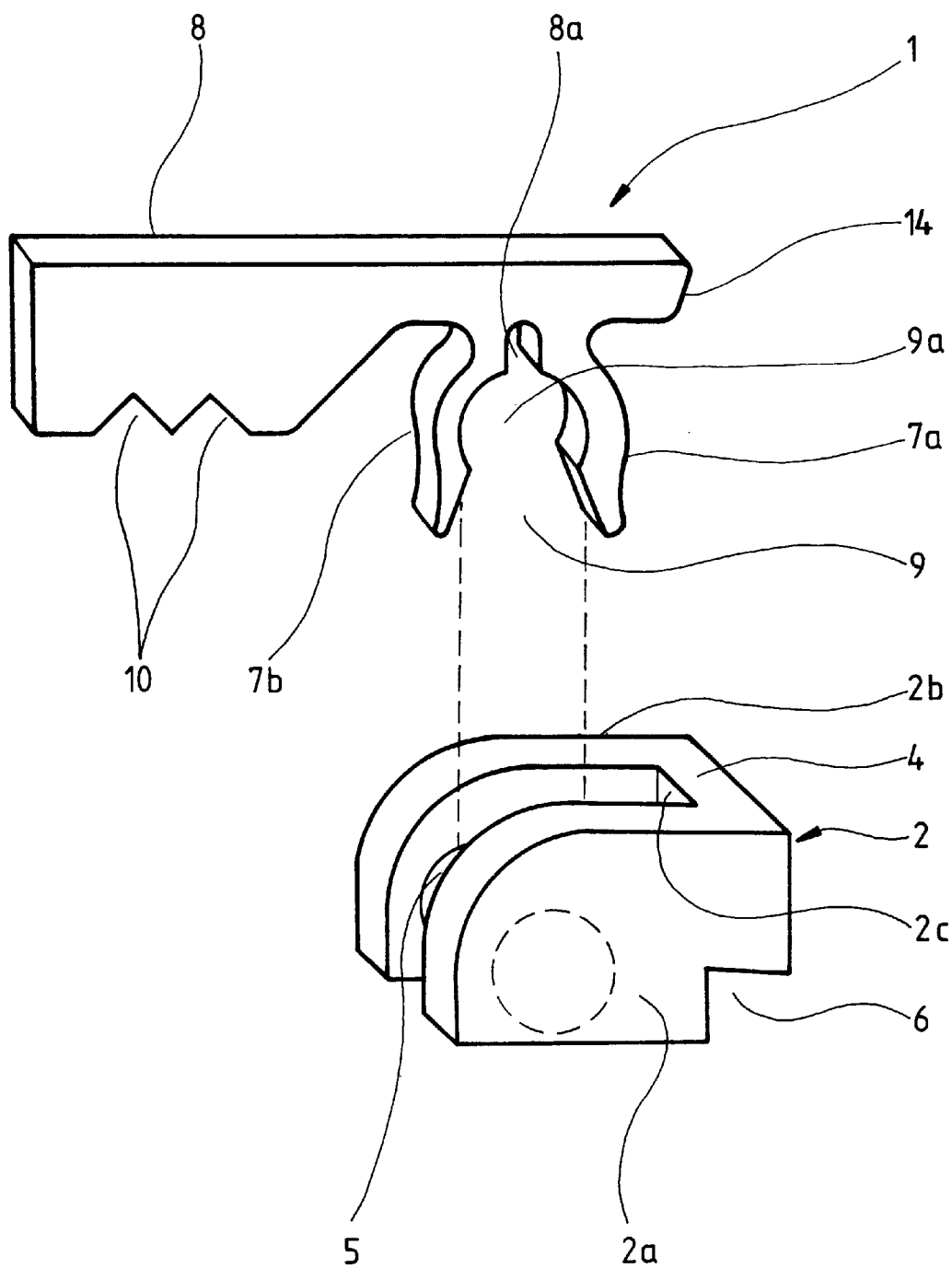
Figure 4:
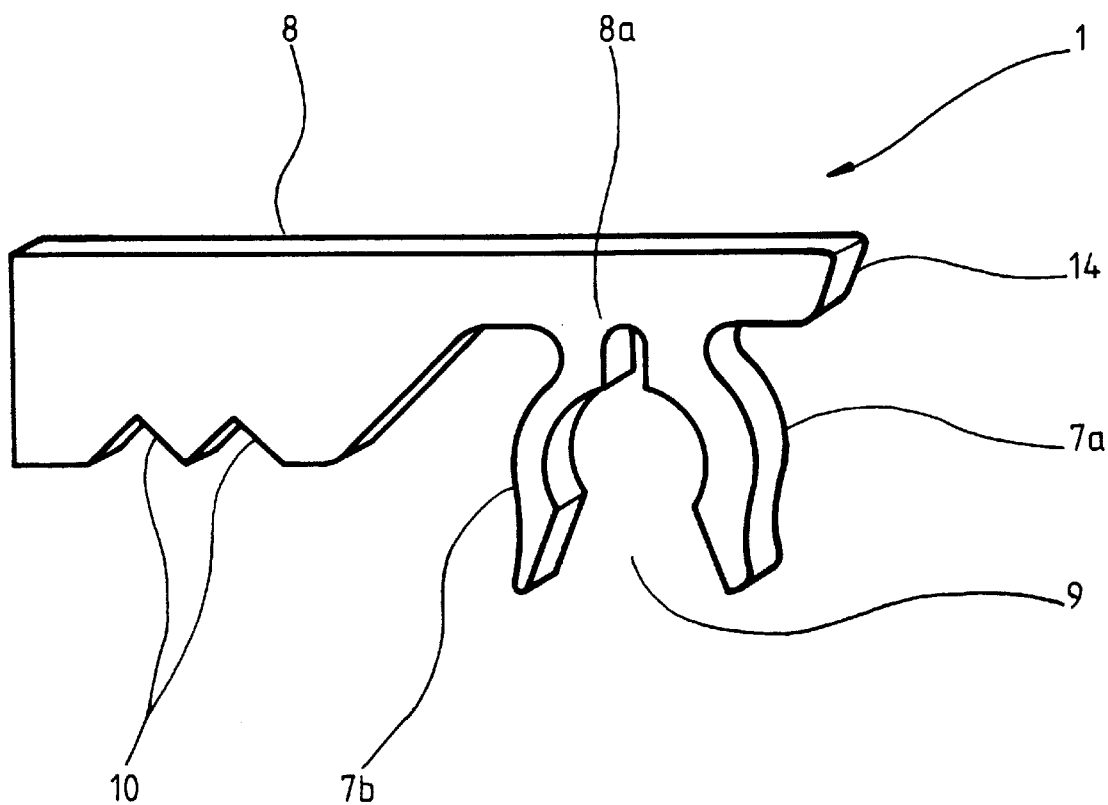
FIG. 4 shows a cross sectional view of the male portion of the precision attachment in accordance with the embodiment of the invention shown in FIG. 1

The male portion 1 of the proposed precision attachment depicted in perspective in FIG. 1 and in section in FIG. 4 comprises a carrier 8 of generally rectangular section with locating slots 10 at the bottom thereof, where male portion 1 is fixedly mounted onto the partial denture when these locating slots 10 are filled with acrylic resin paste means, which is used as binding means of male portion 1 with the partial denture.

Carrier 8 of male portion 1 has a rectangular shape with a linear upper surface, whereas the lower surface thereof is tapered to create a thinned portion 8a, whereupon is fitted the anchorage means 7.

Figure 3:
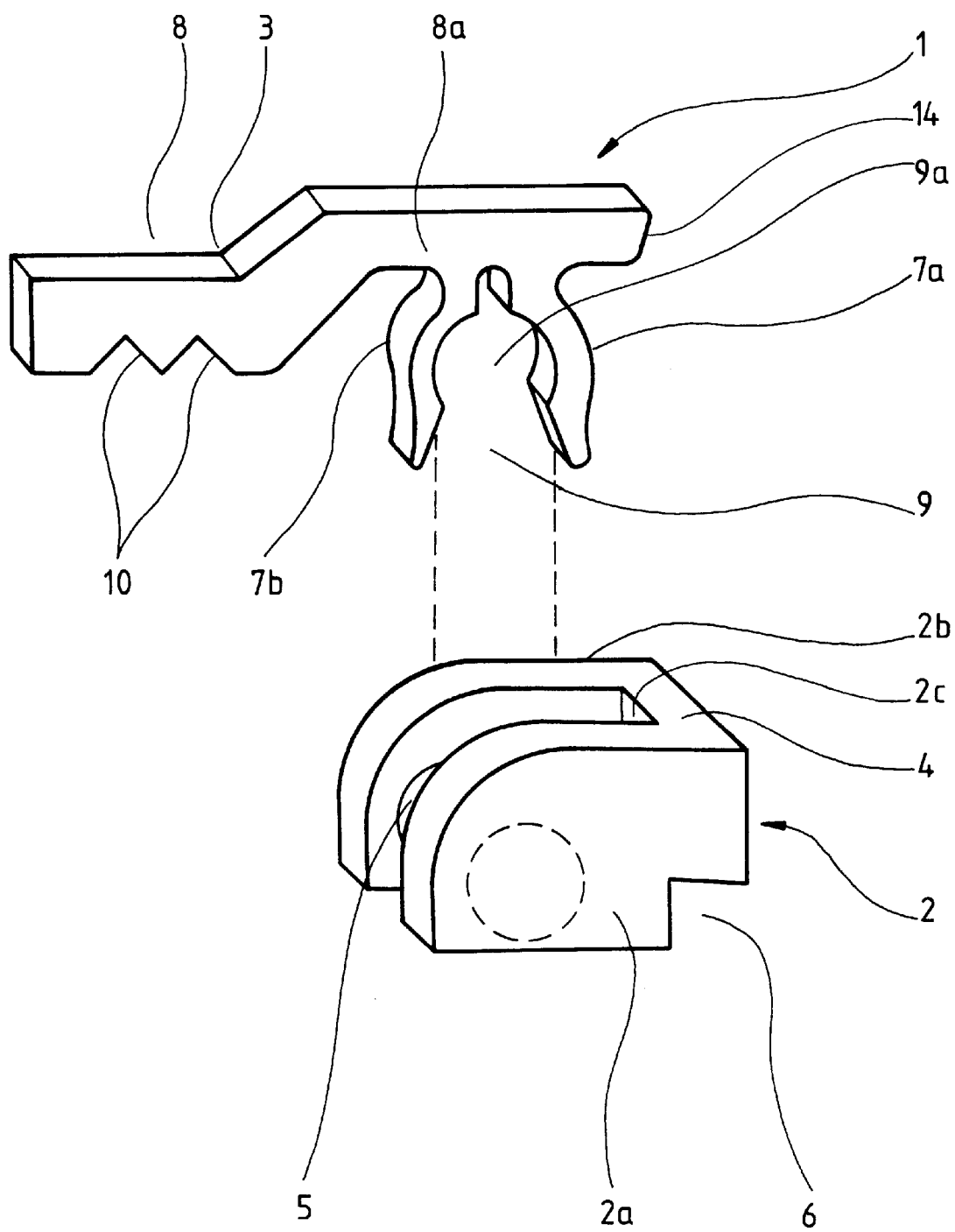
FIG. 3 shows a perspective view of an alternative embodiment of the precision attachment of the invention wherein the carrier portion of the attachment's male portion is cut to an angular section.
Figure 5:
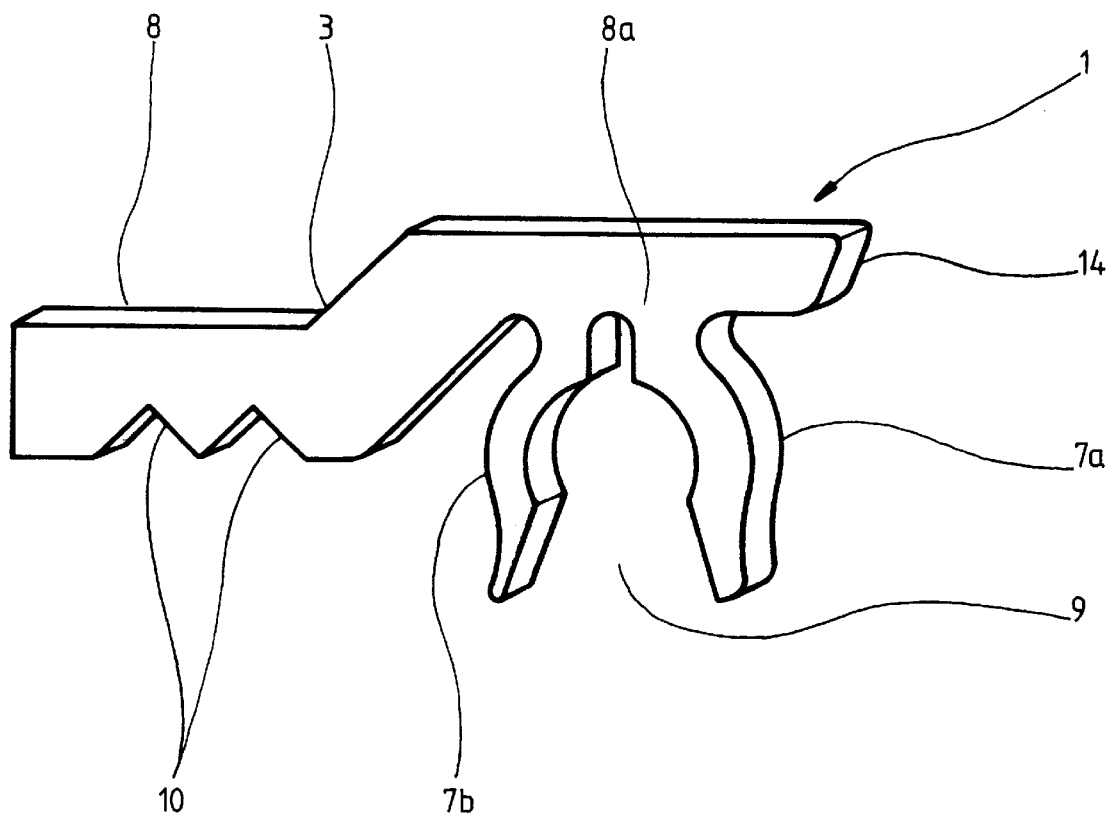
FIG. 5 shows a cross sectional view of the male portion of the precision attachment in accordance with the alternative embodiment of the invention shown in FIG. 3.

In accordance to the alternative embodiment of the invention depicted in perspective in FIG. 3, and in section in FIG. 5 the upper surface of carrier 8 of male portion 1 is cut at an angular section, the peak of the angle denoted by numeral 3, wherein in this way more space becomes available for mounting the male portion 1 of the attachment onto the partial denture shown in FIG. 2 with a base portion 12.

Figure 6:
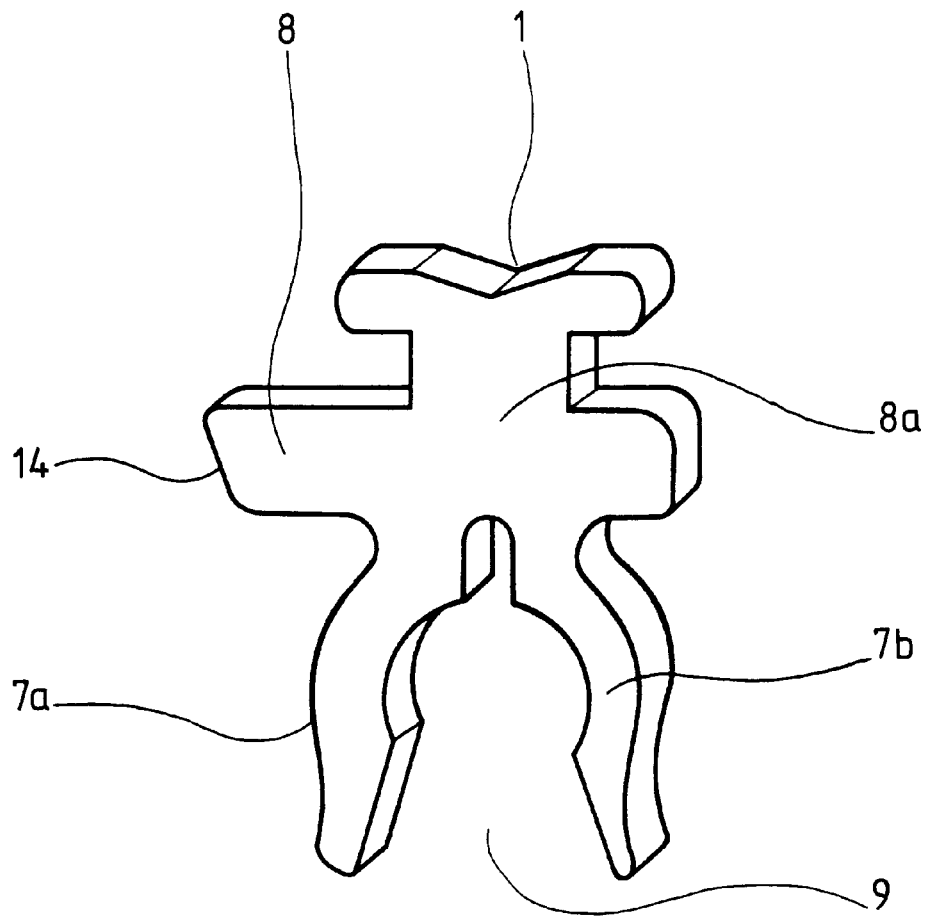
FIG. 6 shows still another cross sectional view of the male portion of the precision attachment in accordance with the alternative embodiment of the male portion of the precision attachment of the invention.

In accordance to the alternative embodiment of the invention depicted in FIG. 6 the longitudinally extending carrier 8 has been removed and instead the upper surface 8 of the anchorage means 7 of the attachment extends to a carrier with locating slots 10 at the top thereof which are again being filled with acrylic resin paste means to mount male portion onto the partial denture.

In either one of the embodiments of the invention shown in FIGS. 1 and 3, the carrier 8 extends to an end projecting thinned portion 8a wherein is formed the anchorage means 7 of the attachment. The horseshoe shaped anchorage means 7 comprises a pair of uniform jaws 7a and 7b, which are initially divergent and subsequently convergent to define a central gap 9a, becoming divergent again to define an entrance gap 9.

The male portion 1 of the precision attachment for a partial denture in accordance with the invention is characterized by facility of mounting onto the partial denture. Contrary to attachments of the prior art which are embodied in the partial denture in a way that their detachment is practically impossible without non reversible damaging effects on the partial denture characteristics, the male portion 1 of the attachment of the present invention is slidably introduced within a suitable gap of the partial denture and can similarly be extracted thereof, since the only region of its fixedly adhesion to the denture is the above mentioned paste of acrylic resin within locating slots 10 of carrier 8,8a. Thus, detachment of male portion 1 from the partial denture if required can be effected by mere scraping of the acrylic resin paste out of locating slots 10 and slidably pulling carrier 8,8a out of the partial denture without causing any damaging effects on the characteristics of the partial denture and without need of repetitive visits to the dentist and repetitive cooperation of the dentist with the dental technician.

In connection to the above, it must however be noted that in comparison to retaining means for partial dentures of the prior art, probabilities of wear and consequently of need of repair or replacement of either the male or female portion of the proposed attachment are considerably reduced and more importantly, if the need arises, any repair work can be done with the aforementioned facility. The most adverse malfunction that may occur in relation to the proposed attachment is loosening of jaws 7a, 7b of male portion 1, which after long repetitive usage may not exert the optimum clipping force around spacer pin 5 of female portion 2. This can be handily corrected by simple tightening of the jaws with conventional pliers.

A further characterizing feature and advantage of the partial denture bearing the proposed precision attachment is related to the ease of inserting and locating the partial denture in the oral cavity. Due to the fact that the partial denture of the invention has eliminated the awkward retaining means extending from one side to the opposite side of the oral cavity and to that it can be supported by unilateral anchorage with sole anchorage means the proposed precision attachment, the partial denture can be inserted in place within the oral cavity in a considerably easier manner, since it is merely needed to locate one single point, i.e. the point at which jaws 7a, 7b of anchorage means 7 grip spacer pin 5 of female portion 2 of the attachment of the invention. When this happens, male portion 1 is firmly connected with female portion 2, as spacer pin 5 of female portion 2 passes through the entrance gap 9 and fits in place within central gap 9a of anchorage means 7 of male portion 1 by means of a slight downward push of the latter, wherein it is firmly held by jaws 7a, 7b. Detachment of the partial denture is easily effected when male portion 1 is pulled upwards to extract anchorage means 7 from spacer pin 5.

Engagement relationship of male portion 1 and female portion 2 of the proposed attachment is such as to allow unidirectional freedom of movement, in particular a specified within a certain predetermined range freedom of rotation of the anchorage means 7 of male portion 1 around spacer pin 5 of female portion 2. The range within which freedom of rotation of the anchorage means 7 around spacer pin 5 is allowed, is defined by means of an angular edge 14 of the end projecting thinned portion 8a of male portion 1 and a correspondingly cut edge 4 at the upper surface of laterally extending wall 2c of female portion 2. Rotation of anchorage means 7 around spacer pin 5 stops when angular edge 14 of male portion 1 comes to matching contact with the correspondingly cut edge 4 of female portion 2.

Besides from the above mentioned freedom of rotation within a certain predetermined range of anchorage means 7 around spacer pin 5, the male portion 1 cannot move in any other direction with respect to female portion 2. In particular, male portion 1 is restricted from longitudinal back and forth movement with respect to female portion 2 due to the tight grip of spacer pin 5 by jaws 7a, 7b of anchorage means 7 and is also restricted from sideways, right or left, movement due to the fact that jaws 7a, 7b of anchorage means 7 have a width corresponding to the length of spacer pin 5 and thereby anchorage means 7 is sideways confined by parallel side walls 2a, 2b of female portion 2, the distance of side walls 2a, 2b being equal to the length of spacer pin 5. It is obvious therefore that the partial denture employing the precision attachment of the invention presents the above unidirectional freedom of movement with respect to supporting teeth and is restricted from moving in any other direction.

The precision attachment of the invention exhibits strain absorber properties, since during mastication the extending end 8a of male portion 1 moves through the exerted pressures to carry out the above mentioned unidirectional movement, so as to achieve relief of strains being applied at the one or more supporting teeth.

The precision attachment described herein above can be offered in a variety of designs which however do not depart from the inventive step disclosed herein. By way of example, each one of jaws 7a, 7b of anchorage means 7, may be divided in two or more parallel portions, their combination resulting to the same effect of the anchorage means depicted in the drawings. Design variations may be made in either one or both of the male portion 1 and female portion 2 of the attachment of the invention.

It is therefore noted that the herein above description of the invention was made by reference to illustrative but not confining embodiments. Various changes or amendments may be made relating to forms, dimensions, materials and accessories used in the assembly process, which as long as they do not comprise a new inventive step, are considered part of the scope and aims of the present invention.

I claim:

1. Precision attachment adapted to be used for a partial denture with unilateral anchorage, said precision attachment being the sole supporting means for said partial denture, comprising a female portion for being fixedly mounted onto a crown surrounding at least one supporting tooth, said female portion comprising a pair of parallel side walls interconnected by a laterally extending wall, said laterally extending wall adapted to be fixedly mounted onto said crown surrounding at least one supporting tooth, said parallel side walls having upper surfaces following a uniform curvature and linear bottom surfaces, said linear bottom surfaces of each one of said parallel side walls including curved recessions, said recessions inhibiting hazardous contact of said female portion with underlying gums, a spacer pin interconnecting said parallel side walls of said female portion;

a male portion for being mounted onto said partial denture, said male portion comprising a longitudinally extending carrier, said carrier being of rectangular shape with locating slots at the bottom side thereof, said carrier adapted for slidably inserting within a suitably formed gap of said partial denture and for being fixedly mounted therein by filling said locating slots with acrylic resin paste, a thinned end of said carrier bearing an anchorage means adapted for being projected outward from said partial denture, said anchorage means having a horseshoe form extending downward from said thinned end of said carrier, said anchorage means including a pair of uniform initially divergent and subsequently convergent jaws, a central gap being defined between said initially divergent and subsequently convergent jaws, wherein said male portion is removably connected to said female portion when said thinned end of said carrier of the male portion is inserted within a receiving cavity formed between said parallel side walls of the female portion and said pair of jaws of said anchorage means come to a gripping contact with said spacer pin, said spacer pin being locked within said central gap between said jaws, said anchorage means being rotatable around said spacer pin within a predetermined range of rotation, said anchorage means having a width corresponding to the length of said spacer pin thereby inhibiting lateral movement of said anchorage means within said receiving cavity of the female portion.

2. The precision attachment according to claim 1, wherein said thinned end of said carrier of the male portion adapted for being projected outward from said partial denture includes an angular edge and said laterally extending wall of said female portion includes an upper surface with an angularly cut edge, said angular edge of said thinned end of said carrier of the male portion coming into matching contact with said angularly cut edge of the upper surface of said laterally extending wall of the female portion, thereby defining a position of termination of rotation of said anchorage means of the male portion around said spacer pin of the female portion within said predetermined range of rotation.

3. The precision attachment according to claim 1, wherein said longitudinally extending carrier adapted for slidably inserting within said partial denture and said thinned end of said carrier of the male portion adapted for being projected outward from said partial denture have a co-linear upper surface.

4. The precision attachment according to claim 1, wherein said longitudinally extending carrier adapted for slidably inserting within said partial denture has a linear upper surface and said thinned end of said carrier adapted for being projected outward from said partial denture has a linear upper surface, said linear upper surface of said thinned end of said carrier being parallel and elevated with respect to said linear upper surface of said carrier which is adapted for being inserted within said partial denture to allow more space for slidably inserting said longitudinally extending carrier of said male portion into said partial denture.

5. A partial denture with unilateral anchorage being supported by means of a precision attachment, without said partial denture being counter-supported at the opposite side of the oral cavity, said precision attachment being the sole supporting means for said partial denture and comprising a male portion and a female portion, said female portion being adapted to be fixedly mounted onto a crown surrounding at least one supporting natural tooth, said female portion comprising a pair of parallel side walls interconnected by a laterally extending wall, said laterally extending wall being fixedly connected to said crown and said pair of parallel side walls being projected thereof forming a receiving cavity with a spacer pin interconnecting said parallel side walls, said male portion comprising a longitudinally extending carrier, said carrier being slidably inserted within a suitable gap of said partial denture and being fixedly mounted therein by means of acrylic resin paste filling of locating slots at the bottom thereof, an end projecting thinned portion of said carrier being provided with an anchorage means adapted to be inserted within said receiving cavity of said female portion during insertion in place of said partial denture, said anchorage means comprising a pair of initially divergent and subsequently convergent uniform jaws, a central gap being defined between said pair of initially divergent and subsequently convergent uniform jaws, said jaws being applied around said spacer pin of said female portion during insertion in place of said partial denture, said spacer pin entering within said central gap and being retained therein, wherein when in place said partial denture exhibits a unidirectional freedom of movement in a vertical upward-downward direction during mastication as said anchorage means rotates around said spacer pin, wherein said jaws effect a tight grip around said spacer pin and thereby restrict said male portion from longitudinal back and forth movement with respect to said female portion and wherein said jaws have a width corresponding to the length of said spacer pin and thereby restrict said male portion from sideways right-left movement with respect to said parallel side walls of said female portion.

* * * * *